United States Patent [19]

Yu et al.

[11] Patent Number: 5,131,752
[45] Date of Patent: Jul. 21, 1992

[54] METHOD FOR FILM THICKNESS ENDPOINT CONTROL

[75] Inventors: Chorng-Tao Yu, Yorba Linda; Kenneth H. Isaak, Tustin, both of Calif.

[73] Assignee: Tamarack Scientific Co., Inc., Anaheim, Calif.

[21] Appl. No.: 545,997

[22] Filed: Jun. 28, 1990

[51] Int. Cl.$^5$ .............................................. G01J 4/00
[52] U.S. Cl. .................... 356/369; 356/382; 427/10; 156/626
[58] Field of Search ............ 356/364, 366, 367, 368, 356/369, 381, 382; 250/225; 156/626; 427/10

[56] References Cited

U.S. PATENT DOCUMENTS

| | | | |
|---|---|---|---|
| 3,158,675 | 11/1964 | Murray et al. | 88/14 |
| 4,105,338 | 8/1978 | Kuroha | 356/118 |
| 4,649,261 | 3/1987 | Sheets | 219/390 |
| 4,695,162 | 9/1987 | Itonaga et al. | 356/369 |
| 4,698,486 | 10/1987 | Sheets | 250/492.2 |
| 4,837,603 | 6/1989 | Hayashi | 356/369 |
| 4,850,711 | 7/1989 | Sano et al. | 356/382 |
| 4,906,844 | 3/1990 | Hall | 250/225 |

OTHER PUBLICATIONS

"In Situ Film Thickness Monitoring in CVD Processes" Severin and Severijns, Journal of Electrochemical Society, vol. 137, No. 4, Apr. 1990, pp. 1306-1309.
Article "In Situ Ellipsometry During Plasma Etching on SiI$_2$ Films on Si" by Haverlag, et al.; Journal of Vac Society Technology B7 (3) May/Jun., 1989; American Vacuum Society.
Article "Surface Analysis During Vapor Phase Growth", by Hottier and Theetan; Journal of Crystal Growth 48(1980) pp. 644-654.

Primary Examiner—Richard A. Rosenberger
Attorney, Agent, or Firm—Poms, Smith, Lande & Rose

[57] ABSTRACT

Endpoint control of thickness of a film being deposited or etched is achieved by use of an ellipsometer that derives delta and psi coordinates of a polarized light beam reflected from the work piece during the course of processing. Measured film thickness is a function of the delta and psi coordinates and other parameters. Delta and psi coordinates of a selected end point (final film thickness) of the process are calculated, and an unbounded line through the endpoint perpendicular to the direction of a plot of delta and psi coordinates adjacent the endpoint is defined. As the processing continues, an ERROR is generated that becomes zero when measured delta and psi coordinates are on the line. When this error changes sign, in the appropriate cycle and within a reasonable range of the endpoint, the desired thickness has been attained, and the process is stopped. The improved film thickness endpoint control is used in a rapid thermal processing system wherein temperatures are changed at a rate of 100° C. or more to deposit or etch film on a substrate. Instead of using a fixed time and other fixed parameters to control film thickness, the described precision endpoint control is employed to obtain increased accuracy of control of the rapid thermal processing system.

37 Claims, 6 Drawing Sheets

METHOD FOR FILM THICKNESS ENDPOINT CONTROL

BACKGROUND OF THE INVENTION

The present invention relates to the growth or removal of thin films, and more particularly concerns improved methods and apparatus for obtaining films of more precisely controlled thickness.

Thin film growth and etching are widely employed in many fields such as the manufacture of electronic circuits and components. Among other fields employing thin films is the entire field of optics where lenses and other optical components are coated with thin films to obtain various optical properties such as light transmission and reflection. Multi-layer non-reflective thin films or coatings are commonly used.

Film growth and etching process control typically requires the monitoring of a number of variables, such as temperature, pressure, gas flow rates and the like. Monitoring of such variables is performed by conventional sensors and controlled by known open and closed loop control methods to maintain repeatability. When the various parameters are precisely known and controlled, the desired film thickness is obtained by operating the process over a fixed period of time, assuming that the growth or etching rate remains constant with the constant parameters. However, sensor accuracy changes with time and, therefore, process repeatability is degraded. It is critically necessary to repetitively recalibrate the sensors in order to maintain satisfactory process performance. Further, sensitivity margins of some process variables may be lacking in some film growth and etching rates. These sensitivities include temperature effects on growth rate and effects of total area to be etched upon etching rate. Absence of such sensitivity margins makes the fixed time control methods less reliable.

To overcome these problems attempts have been made to employ various types of in-situ film thickness sensing in an effort to obtain direct endpoint control. Among several different methods of in-situ film thickness sensing is the technique known as ellipsometry. Ellipsometry, at present, is a well established method of thin film thickness measurement. By illuminating a sample with monochromatic light having a controlled state of polarization, and then analyzing the polarization state of the reflected light, ellipsometry gives direct access to optical constants of the surface under investigation. When the surface is covered by thin layers of film, both thickness and refractive index of the thin films can be obtained.

The state of polarization of light is defined by the phase and amplitude relationship between two component plane waves, that which is in the plane of incidence and that which is normal to the plane of incidence, into which the electric field oscillation is resolved. The effect of reflection of light from a surface is characterized by the angle delta, defined as the change in phase, and the angle psi, which is the arc tangent of the factor by which the amplitude ratio changes. Ellipsometry measures these quantities, delta and psi. From these quantities one can obtain optical constants of the reflecting material or the thickness and optical constants of the film, such as the index of refraction for transparent films and both index of refraction and the extinction coefficient for absorbing films. Ellipsometry is known to be sensitive to changes in film thickness down to one angstrom and is totally nondestructive. Recent development of automatic ellipsometers, which allow rapid sampling rates to monitor reaction dynamics, provides a basis for in-situ film thickness endpoint control.

Various techniques have been tried in attempts to use in-situ ellipsometry for endpoint control. It has been suggested to calculate a distance between a measured point and a set point to define an error. When the error is smallest, the objective has been reached. However, this method is very difficult to implement in real time. An alternative method, described more particularly below, calculates a variation value empirically or theoretically and compares this variation to the error to stop the process when the error is less than the selected variation. However, if the variation selected is too small the process may never be terminated, whereas if the selected variation is too large the process may be prematurely terminated.

End point control of film thickness is useful in many different types of film growth and etching process control systems and apparatus. One type of such film growth and etching processing is rapid thermal processing (frequently referred to as RTP). This type of processing is employed in the semiconductor industry for semiconductor wafer processing operations, such as implant, annealing, chemical vapor deposition (CVD) of dielectric and polycrystalline silicon films, silicide formation, and many others. Rapid thermal processing has many advantages over conventional batch furnace processing operations, including low thermal mass wafer heating and cooling using a lamp source, short thermal transients (fast heat up and cool down rates), small process chamber volume, and selective wafer heating for cold wall operation. It is compatible with real time, in-situ processing sensors, and is essential for some types of integrated processing.

In rapid thermal processing, system temperature ramp rates are typically on the order of 100° C. per second, and thus optical pyrometry is most commonly employed for temperature control. However, even with extensive and careful calibration of temperature measuring instrumentation, the temperature measurement is subject to significant error. The external pyrometer is dependent for its measurement on surface emittance of the wafer which in turn depends on quality of the wafer as well as thickness of any growing film in a CVD process. Particularly for processing silicon wafers, normal error sources of the pyrometer include temperature dependence of the emissivity of silicon, and variations in wafer surface roughness. Accordingly, uncorrected pyrometer measurements can be in error by as much as 100° C. in a CVD process. Where the RTP process employs a conventional fixed process time control, this temperature error can result in a changing deposition rate and thereby a large deviation in final film thickness. Various calibration schemes, attempting to compensate for variations in emissivity and wafer conditions, can improve reliability and accuracy of pyrometer measurements but have not yet provided a truly acceptable method for RTP process control with good process repeatability. The RTP process still is essentially open loop, depending upon a fixed time and maintenance of precise process parameters.

Accordingly, it is an object of the present invention to provide methods and apparatus which avoid or minimize the above mentioned problems.

SUMMARY OF THE INVENTION

In carrying out principles of the present invention in accordance with a preferred embodiment thereof, thickness of a film or film portion on a substrate is controlled in a process for film growth or film etching by positioning a substrate in a chamber, controlling environment within the chamber so that film will be formed or etched, and measuring parameters of the film. The measuring of film parameters includes the computing of delta and psi coordinates of polarized light reflected from the processed object, determining, in a delta and psi coordinate system, the coordinates of an end point of desired thickness, defining a control line through the end point, generating an error signal indicative of the relation between the line and points defined by measured delta, psi coordinates, and using the error signal to terminate the process. More specifically, there is computed from measured delta and psi coordinates an error that changes sign at the desired point of process termination. A change of the error sign is used to stop the process. The delta and psi coordinates are generated from reflected polarized light.

As applied to rapid thermal processing, the method of the invention includes heating the substrate at a high ramp rate in a rapid thermal processing chamber while monitoring substrate temperature with a temperature sensing device. However, instead of employing a fixed time to control process termination, an error signal indicative of relation of the control line and a point defined by the measured coordinates is employed to terminate the process.

DETAILED DESCRIPTION OF THE INVENTION

Figure 1:
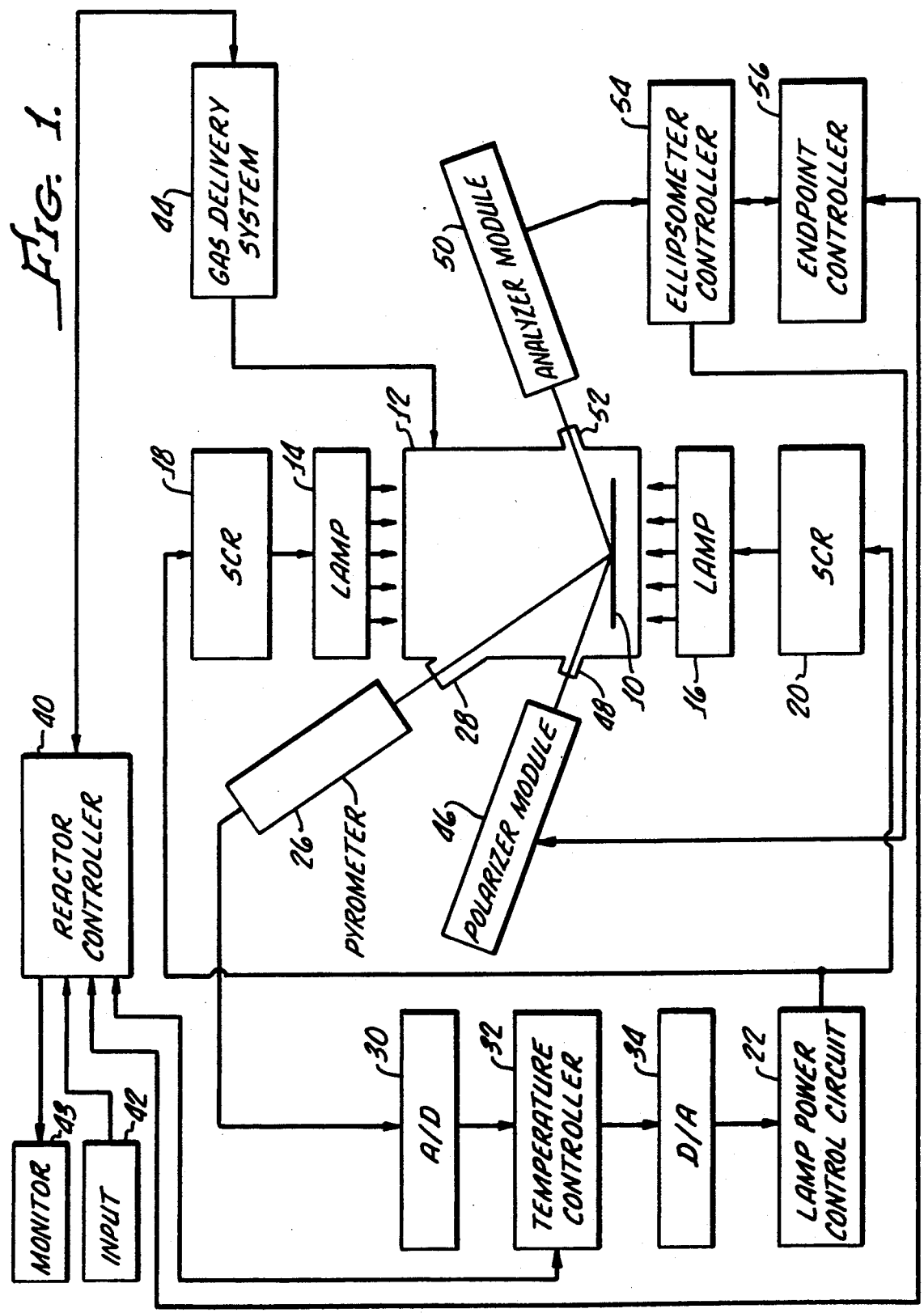
FIG. 1 is a block diagram of a system employing principles of the present invention for in-situ endpoint control of a film growth or etching process.

Illustrated in FIG. 1 is a simplified block diagram of apparatus that may be used in a thin film thickness endpoint control system of the present invention. Many different processes for thin film growth or etching, semi-conductor and other electronic devices and for optical and other devices (several of which are set forth below), may advantageously utilize the film thickness endpoint control of the present invention. However, the invention has been initially implemented in connection with growth of a silicon dioxide film upon a silicon substrate in controlled atmosphere chamber and, accordingly, will be described as it has been used in such a process. As shown in FIG. 1, an exemplary apparatus for carrying out silicon dioxide film growth, or etching (in-situ oxide cleaning), upon a silicon wafer 10 includes a reactor chamber 12 having heating lamps 14,16 under control of silicon rectifier control circuits 18,20 which receive power from a lamp power control circuit 22. Lamps 14,16 are optically coupled to a workpiece (wafer 10) supported in the chamber on a suitable support (not shown) to effect relatively uniform heating of the workpiece. The optical coupling means is formed by the body of the chamber 12.

Temperature control is provided by a closed loop control system including an optical pyrometer 26 sensing radiation emitted from the heated wafer 10 through a suitable window 28 in the wall of reactor chamber 12 and feeding information via an analog to digital converter 30 to a temperature controller 32. The temperature controller sends control signals to the lamp power circuit 22 via a digital to analog converter 34. A reactor controller 40, which is the central controller for the entire processing, receives information, such as desired endpoint thickness and various desired parameters of the process, from an input device 42 and provides suitable output displays to the operator at a monitor 43. The controller also exchanges information with the temperature controller 32. A gas delivery system 44, receiving control setpoints from the controller 40, sends a suitable atmosphere or flow of gas into the interior of the chamber 12. Reactor controller 40 may be a personal computer with suitable input devices 42, including a keyboard and display monitor 43 and including other data storage devices.

The reactor controller performs the usual functions of process parameter input, calibration data input, status check, gas delivery system control, detection of alarm or abort conditions, and also controls an in-situ ellipsometer that measures and transmits data for process termination.

The invention has been initially implemented utilizing a reactor chamber of the type shown in U.S. Pat. Nos. 4,649,261 for Apparatus for Heating Semiconductor Wafers In Order To Achieve Annealing Silicide Formation, Reflow of Glass, Passivation Layers, etc., and U.S. Pat. No. 4,698,486 for Method of Heating Semiconductor Wafers In Order To Achieve Annealing Silicide Formation, Reflow of Glass, Passivation Layers, Etc., to Ronald E. Sheets, inventor, both assigned to the assignee of the present invention The disclosures of these patents are incorporated herein by this reference as though fully set forth.

Briefly, the reactor chamber shown in these patents comprises a hollow integrating light pipe in the form of a kaleidoscope, extending to the workpiece support, and which encloses a source of radiant thermal energy (lamps 14,20) which are so arranged as to achieve efficient and substantially uniform heating across the light pipe at a workpiece, such as wafer 10, in a target plane. The light pipe, preferably having an aspect ratio of at least 1, has closed ends to heat the workpiece from both sides uniformly and efficiently, and may employ CW lamps, pulse lamps, or a combination of the two. The apparatus affords rapid thermal processing and will provide temperature increases of as much as 100° C. or more per second, rapidly raising the temperature of the wafer 10 to a suitable processing temperature, such as 1,000° or 1,100° C. for formation of a silicon dioxide film on a silicon substrate, for example.

In a present embodiment of the invention the reactor chamber has a hexagonal cross sectional configuration, such as is illustrated in FIG. 13 of each of the afore mentioned patents to Ronald E. Sheets.

The system illustrated in FIG. 1 employs in-situ ellipsometer endpoint control according to principles of the present invention. A high speed ellipsometer, which may be, for example, a Rudolph Research i1000 In-situ Ellipsometer, manufactured by Rudolph Research of Flanders, N.J., employs a polarizer module 46 which conventionally includes a light source, a polarizer, and a compensator to send polarized light through a window 48 formed in one side of the reactor chamber wall. An analyzer module 50 of the ellipsometer includes an analyzer and photo detector receiving light reflected from wafer 10 through a second window 52 formed in the reactor wall and feeds information to an ellipsometer controller 54 which controls polarizer module 46. Information obtained by the ellipsometer controller 54 is transmitted to an endpoint controller 56 embodying principles of the present invention. Controller 56 may be a personal computer or a single circuit board programmed to carry out the method to be described herein, and receives certain information from reactor controller 40.

The light source of the ellipsometer is a monochromatic collimated polarized light which may be any wavelength from ultraviolet to the far infrared A helium/neon laser with a standard wavelength of 632.8 nanometers has been employed. As compatible with the high speed data sampling that is carried out by the ellipsometer, the polarizer, compensator and analyzer can be either stationary or rotating In an initial embodiment a fixed polarizer and rotating compensator, together with a fixed analyzer combination, has been used. If deemed necessary or desirable, an auto collimator and microscope (not shown) can be employed with the analyzer module 50 to facilitate optics alignment and allow a sample 10 to be viewed. Ellipsometer electronics and control module 54 includes an ellipsometer power supply, a speed controller for the rotating compensator, a control microprocessor, and an interface for transmission of data (delta and psi) to endpoint controller 56.

Both polarizer and analyzer modules 46,50 are mounted outside of the reactor chamber 12 so that the window ports 48,52 will allow transmission of the light beam from the module 46 to reach the vicinity of the center point of wafer 10 inside the chamber 12 and then to be reflected to the analyzer module 50. Wafer 10 is precisely located inside the chamber with the film side up, facing the light beam, to ensure repeatable alignment. The angle between a normal line to the wafer surface and the axes of the window ports is preferably 70°, although values between 40° and 85° may be used for many applications. Thin film measurement by means of ellipsometry can be performed upon samples in normal air or other gaseous environments, as well as in a vacuum. Therefore the interior of the reactor chamber 12 can be under vacuum or atmospheric pressure. Optics materials for windows 48,52 are selected to be compatible with the wavelength of the light source of polarizer module 46.

Endpoint controller 56 receives a command signal from the system reactor controller 40 to begin endpoint checking upon start of a process. It then directs ellipsometer controller 54 to perform measurements and transmit delta and psi data for calculation of a process controlling error value and determines when to stop the process, as will be described more particularly below. If the process has reached the endpoint, the endpoint controller returns a signal to reactor controller 40 to terminate the process or to execute the next processing step.

A fundamental advantage of the present invention is to enable the process to be precisely stopped when film thickness has attained a desired value.

It is known, of course, to calculate the endpoint, which is the desired film thickness. Endpoint data (delta and psi values of a film having the desired thickness) for such thickness, De, Pe, (where De and Pe are delta and psi coordinates of the calculated endpoint) can be conventionally calculated from the known angle of incidence (AOI), wavelength of the light source, final (desired) film thickness, and optical constants of the substrate and film at the process temperature. In a manner analogous to use of a conventional set point, the calculated endpoint data is used, in one prior art method, as the control set point, and the distance between the set point and a measured data point (Dm, Pm), where Dm and Pm are measured delta and psi values, is used as the error. This may be expressed as follows:

$$\text{ERROR} = \text{DISTANCE} = \sqrt{(Dm - De)^2 + (Pm - Pe)^2} \qquad \text{Eq. (1)}$$

Utilizing the predicted endpoint and measured data in this manner, one looks for the measured data point with the smallest error, that is, the data point that is closest to the set point. However, this method is very difficult to implement in real time. In such a situation, since the minimum value of the error is not known initially, the error must be allowed to decrease and then to increase again before the minimum can be identified. Furthermore, in this method instrument noise adds more complexity to the method of searching for a minimum error.

In an alternative method of the prior art a variation value is selected and used to determine the condition required to stop the process. Such a variation value can be determined empirically or can be calculated theoretically by modeling all variations of thickness, temperature, angle of incidence and related parameters and then selecting the greatest distance or greatest variation in the delta-psi plane or delta-psi coordinate system. The delta-psi plane, of course, is the plane of the plot of delta generally plotted vertically against psi, generally plotted horizontally. In employing this prior art variation method, the variation must be great enough to accommodate all of the possible system variations. The greatest variation on the delta-psi plane is not just the maximum of each parameter as it is varied independently, but it is the worst combination of all such variations. The greatest distance on the delta-psi plane is then selected by:

$$\text{VARIATION} = \sqrt{(Dv - De)^2 + (Pv - Pe)^2} \qquad \text{Eq. (2)}$$

where Dv and Pv are the delta and psi coordinates of one end of the greatest distance line, and De and Pe are the delta and psi coordinates of the precalculated endpoint In this method the process is stopped when the error is smaller than the pre-selected variation. The error is still computed as set forth in equation 1, but instead of stopping the process when a minimum value of the error is reached, the error is continuously compared with the preselected variation, and when the error becomes less than the variation the process is stopped.

Figure 2:
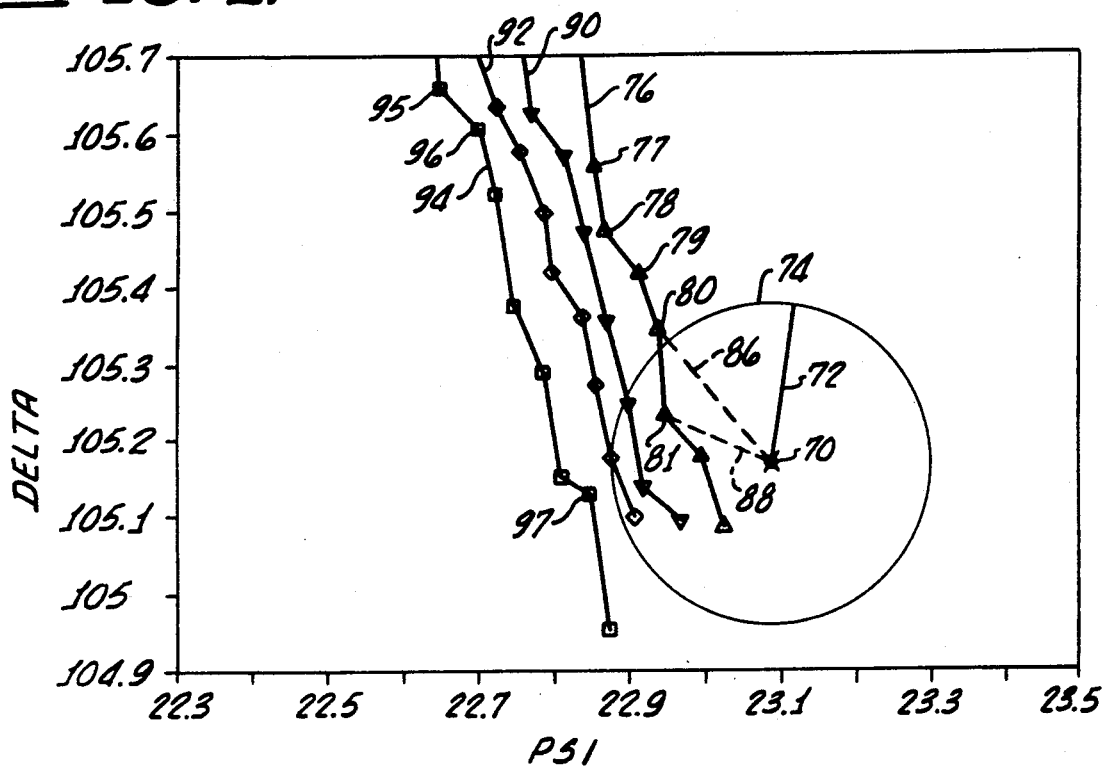
FIG. 2 is a graphic illustration useful in describing a method of the prior art that employs ellipsometry for film thickness endpoint control.

Application of this prior art process of using a precalculated variation to stop the process is graphically illustrated in FIG. 2. In FIG. 2 four process runs are used to explain the prior art method, although the method was not actually used in these runs. It may be noted that the process runs shown in FIG. 2 are the runs shown in FIG. 3 which will be described below in explaining an example of use of the present invention. FIG. 2 is a graphic plot of four different actual process runs of a process in which a silicon dioxide film was formed on a silicon substrate employing apparatus of the type illustrated in FIG. 1 and described in the patents identified above. As mentioned above, the described prior art method was not used to stop these processes. For these process runs, delta and psi coordinates of the desired endpoint 70 (delta=105.167, psi=23.088) was calculated from the following parameters:

| Wavelength | 6328 Angstroms |
|---|---|
| Angle of incidence | 70.06° |
| Temperature | 1,100° C. |
| Ambient (Air in the Chamber) | 1 (N - Index of Refraction) |
| | 0 (K = Extinction Coefficient |
| Film | (SiO2) 1.486 (N at 1,100° C.) |
| | 0 (K at 1,100° C.) |
| Substrate (si) | 4.421 (N at 1,100° C.) |
| | 0.260 (K at 1,100° C.) |
| Film Thickness | 400 Angstroms |

In the process of which results are graphically depicted in FIG. 2, it was desired to grow a 400 Angstroms thick silicon dioxide film on a 100 millimeter diameter silicon wafer using 0.5 standard liters per minute (SLPM) of oxygen gas under atmospheric pressure conditions. Results of four actual process runs near a calculated endpoint 70 are plotted in FIG. 2. As previously mentioned, a variation is hypothetically determined having a length as indicated by the line 72, which thus defines the radius of a circle 74 which is drawn around calculated endpoint 70. As deposition of the silicon dioxide film proceeds the delta and psi coordinates are measured by the above described ellipsometry, and such measurements are plotted for a first run 76 at points such as 77, 78, 79, 80, and 81. If this "variation" method had been used, the process is allowed to continue as long as the error (the distance 86 between endpoint 70 and one of the measured points, such as point 80) is greater than the variation 72. At the next measured point, point 81, the distance 88 between the desired endpoint 70 and the measured point 81 is less than the variation 72, and the process would have been terminated.

Similar process runs under the same conditions are illustrated by the plotted lines 90 and 92. Each of these runs reaches a point at which the error becomes less than the variation, so that, if the prior art method had been employed in the runs of FIG. 2, the process runs would have been terminated within the selected variation of this prior art process.

It must be noted that, even though the process is repeated at ostensibly identical parameters during each of these runs, it is not possible to maintain all of the parameters exactly the same so that the process cannot be precisely repeatable. In particular, as previously mentioned, closed loop control of temperature is performed by a pyrometer which controls the lamp power circuit. However, surface roughness, emissivity of the wafer and other factors may vary widely so that the actual temperature of the wafer will vary from run to run. Despite closed loop temperature control, temperature has been known to vary by as much as 100° C. This temperature variation is a major cause of the variation in the actual measurements made during the several process runs. It is such variations that cause the lateral displacement of curves 76, 90, and 92 relative to one another in the delta-psi plane.

A fourth run made under the presumably identical conditions described above is illustrated by the curve 94 of FIG. 2, and shows measured points 95,96, etc. which successively approach the desired endpoint 70. However, as can be seen in this plot, the closest approach to the endpoint is at a measured point 97, which itself is still outside of the circle 74, so that the distance between endpoint 70 and measured point 97 is still greater than the variation. Accordingly, under the specific conditions of the process depicted by curve 94, the error of the prior art process will never become smaller than the variation, and thus the process will not be stopped when using this method. As mentioned above, use of a greater variation, greater than the selected value of distance 72, would provide a greater diameter circle 74, and thus may allow this method to control a process depicted by line 94. This use of a greater variation might enable this method to be more useful. However, as the selected variation increases, control accuracy decreases, and use of the method employing variation requires an undesirable tradeoff between control accuracy and utility of the control method.

Figure 3:
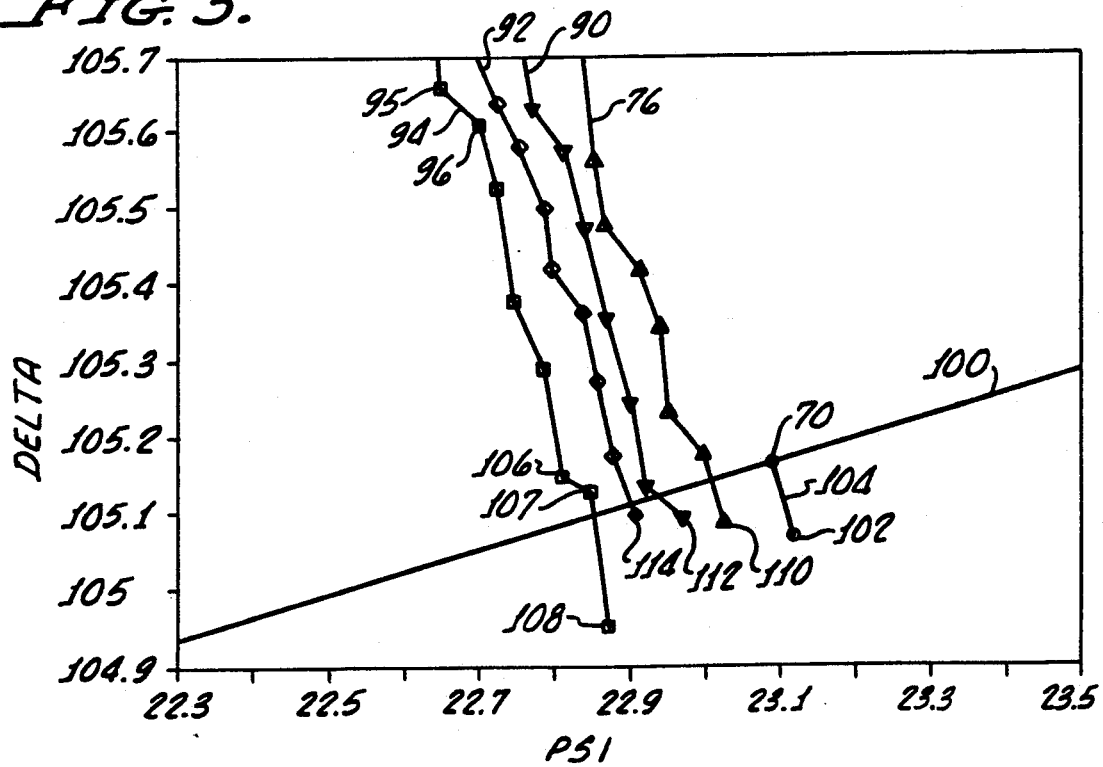
FIG. 3 is a graphic illustration of operation of the disclosed apparatus for endpoint control.

According to principles of the present invention, an endpoint control method is employed which avoids problems of prior methods. A vastly superior method of controlling endpoint thickness is the use of a control line which passes through the desired endpoint. The use of such a control line is illustrated in FIG. 3. FIG. 3 comprises a plot of the same four process runs 76, 90, 92 and 94 as are illustrated in FIG. 2, employing the same process parameters, with the desired endpoint 70 again illustrated in this Figure. However, instead of determining a selected variation, an unbounded control line 100 is selected, passing through the pre-computed endpoint 70 and extending in a direction that is generally transverse to the direction of the extent of the plotted measured points of the several runs. Preferably line 100 is a straight line or nearly a straight line, although a line that is somewhat curved or otherwise deviates from linearity may be employed.

Direction of unbounded control line 100 can be selected to extend in the desired transverse direction by various methods. However, it is most convenient to select a second film thickness slightly greater than the film thickness defined by endpoint 70, such as a second film thickness represented at a point 102. For example, where the target endpoint 70 defines a film thickness of 400 Angstroms (delta and psi coordinates 105.167, 23.088 in this plot), the second point 102 is selected for a 401 Angstrom film thickness, having coordinates 105.068, 23.117. The unbounded control line 100 is then selected as a straight line having a direction perpendicular to a line 104 between the target endpoint 70 and the second film thickness point 102. Line 104 extends in a direction generally parallel to the direction of the curves 76, 90, 92, 94 near the endpoint.

A function of delta and psi, F (delta, psi), is chosen such that the function is zero (F (delta, psi)=0) for all points on the unbounded control line 100. Effectively the chosen function defines the control line. The line is the locus of points for which the chosen function is zero. Thus one can simply calculate the value of this function of measured delta and psi values, Dm and Pm, and stop the process when the value of the function is sufficiently close to zero. Preferably the process is stopped when the value of the function changes sign.

As the measured data points in the delta-psi plane approach the unbounded control line 100, the distance from the measured points to the unbounded control line decreases, and, as the measured data points pass across and move away from (downwardly in FIG. 3) the unbounded control line, the distance increases. This indicates that a sign change can be detected to stop the process at the very first point past the unbounded control line, thereby obtaining significantly increased accuracy. Preferably, instead of directly computing distance to the control line, the value of the chosen function is computed for each measured pair of delta and psi coordinates, thus effectively defining a line through the measured coordinates parallel to the control line. Process termination is then signaled by a change in sign of the value of the computed function. Because of the relatively great extent of the control line, any lateral displacement (along the psi axis) of the plot of measured data points from one run to the next (caused by temperature variation, for example) cannot cause an indeterminate result (as with curve 74 in FIG. 2). This is true because all plots, even those with significant displacements, will still cross the unbounded line. Thus no trade off is required between control accuracy and usefulness of the control method.

In an embodiment that has been implemented and tested, the unbounded control line 100 is generated by initially calculating (De, Pe) of the desired endpoint thickness. Then the coordinates Ds and Ps of a second point of a different thickness are calculated for the same temperature. These are the coordinates of the second point 102, the first pair of coordinates being coordinates of the desired endpoint 70 of FIG. 3. Unbounded line 100 is then defined by constants A,B and C of the Equation:

$$A \times (delta) + B \times (psi) + C = 0 \qquad \text{Eq. (3)}$$

The constants are those for the unbounded line passing through the endpoint 70 and perpendicular to line 104 joining points 70 and 102. For this unbounded line 100, a function, F, of delta and psi coordinates is defined as:

$$F (delta, psi) = 3.4136 \times (delta) - (psi) - 335.91 \qquad \text{Eq. (4)}$$

where constants A, B and C are 3.4136, −1, and −335.91, respectively, for the specific process illustrated in FIG. 3. The constants of this function define the unbounded straight line 100, which passes through the desired endpoint 70 and is perpendicular to the line between points 70 and 102. Any pair of delta and psi coordinates defining a point on the line 100 accordingly meet the condition:

$$F (delta, psi) = 0 \qquad \text{Eq. (5)}$$

The control error of each measured point defined by measured delta and psi coordinates, Dm, Pm, in the delta-psi plane is defined as:

$$ERROR = F(Dm, Pm) = A \times (Dm) + B \times (Pm) + C \qquad \text{Eq. (6)}$$

Thus, as can be seen from Equation (6), when the measured data points in the delta-psi plane, such as points 95, 96, 106 and 107 approach the unbounded control line 100, the magnitude of ERROR decreases (it approaches zero), and the magnitude of error for data points, such as point 108 on the other side of line 100, increases. Thus, ERROR for data points on different sides of the line have opposite algebraic signs. ERROR has different signs on opposite sides of the control line for any slope of the line, whether positive or negative, or horizontal or vertical. A sign change, which can be readily detected, occurs when the value of the function of the measured data points cross the control line. This sign change provides a simple and highly reliable method of detecting the endpoint and is substantially unaffected by noise in the measuring system. The process can be stopped upon occurrence of the very first measured point after crossing the control line. Using a fast data sampling rate, the magnitude of ERROR of the first measured point after the line crossing can be very small.

In the sample of FIG. 3 all of the process runs, namely runs 76, 90, 92 and 94, were terminated at the very first points after crossing the line 100. These points are indicated at 110, 112 and 114 for process runs 76, 90 and 92, and at point 108 for process line 94. The control ERROR values (e.g. values of F(delta,psi)) corresponding to stop points 108, 110, 112 and 114 were respectively −0.519, −0.213, −0.135, and −0.058. These runs indicate the great precision and repeatability of the described method. The data was taken at intervals of 0.7 seconds between measurements, and film thicknesses were respectively 404, 404, 403, and 404 Angstroms, with an average index of refraction of 1.455.

Real time ellipsometry data moves along a locus in the delta psi plane that may have many different shapes. For transparent films these curves can be a closed or open shaped locus depending upon the optical constants of the film. Delta and psi values repeat over each multiple of a periodic thickness. For absorbing films the locus can be spirally shaped or a shifted open shaped locus. Curve 130 of FIG. 4 simulates a silicon dioxide growth process on a silicon substrate at 1,100° C. The following parameters were used to generate this curve:

| | |
|---|---|
| Wavelength | 6328 Angstrom |
| Angle of Incidence | 70° |
| Index of Refraction | 1 (Ambient) 1.486 (Silicon Dioxide Film) 4.421 (Silicon) |
| Extinction Coefficient | 0 (Ambient) 0 (Silicon Dioxide Film) 0.260 Silicon) |

Figure 4:
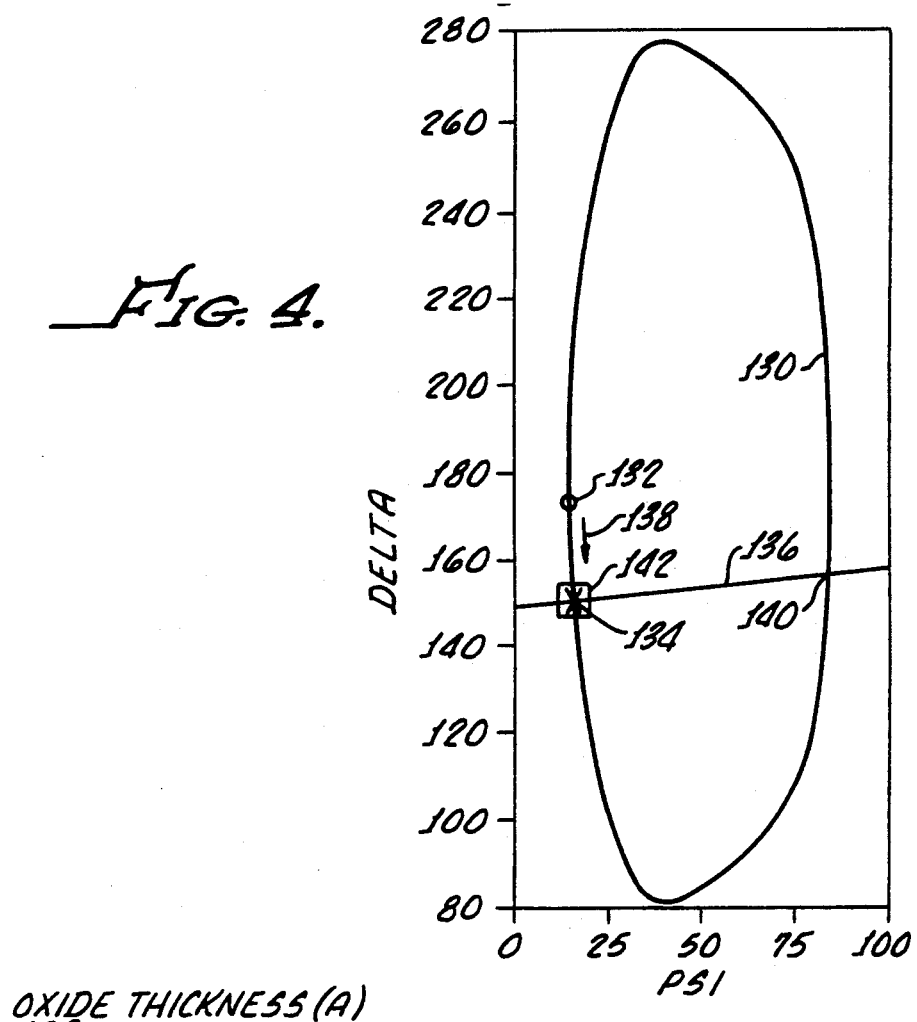
FIG. 4 illustrates the delta and psi locus of a single transparent film and an endpoint crossing line.

The graph in FIG. 4 shows delta varying between 80 and 280 and psi varying between 0 and about 90. A starting point of the process is indicated at point 132 on the locus 130. The starting point indicates the delta and psi coordinates with no oxide film on the substrate (bare silicon). A desired endpoint 134 was calculated for an intended oxide film thickness of 100 Angstroms. An unbounded control line 136 generally transverse to the direction of the locus 130 in the vicinity of endpoint 134 is generated as previously described (e.g. perpendicular to the line between points 70, 102 of FIG. 3). During the film growth process measured data points move along the curve 130 in the direction indicated by arrow 138. In this case, to detect the 100 Angstrom thickness at endpoint 134, there is a first sign change of ERROR, e.g. F(Dm,Pm) as the locus crosses line 136. This first sign change is adequate to conclude that a stop point is reached, as will be explained. For a relatively thick film growth or deposition process, the same stop point 134 can be passed several times before the stop point of the process has been attained, because delta and psi repeat over each multiple of a cycle thickness, which is 2748.6 Angstroms for this model.

Moreover, the unbounded control line 136 intersects the locus curve 130 twice per cycle, once at point 134 and again at a point 140. There will be another sign change of ERROR at the second point 140. Accordingly, to distinguish between the two sign changes, a range verification check is made. This is indicated by the range verification box 142 in the drawing of FIG. 4. The range check is performed by establishing a set of values Dm and Pm that are within a predetermined range of the endpoint values De and Pe so that if a sign change of ERROR occurs when measured values are outside of the selected range, it is known that the sign change does not denote the desired endpoint Only if the sign change occurs when the measured values are within the selected range has the desired endpoint been reached. Of course, as will be described below, for thick films it is also necessary to count the cycles so that the sign change must occur while measured values are within the range and during the proper cycle.

The described control method can be applied for film deposition and also for in-situ oxide cleaning and etching processes. In such cleaning or etching processes the bare silicon condition, indicted by starting point 132, is used as the endpoint, and measured data points move in an opposite direction. In such cleaning and etching processes one might employ a film thickness of a few Angstroms as the endpoint and add a fixed time delay after the attainment of the endpoint (the detected sign change within range and within cycle) to actually stop the process.

Figure 5C:
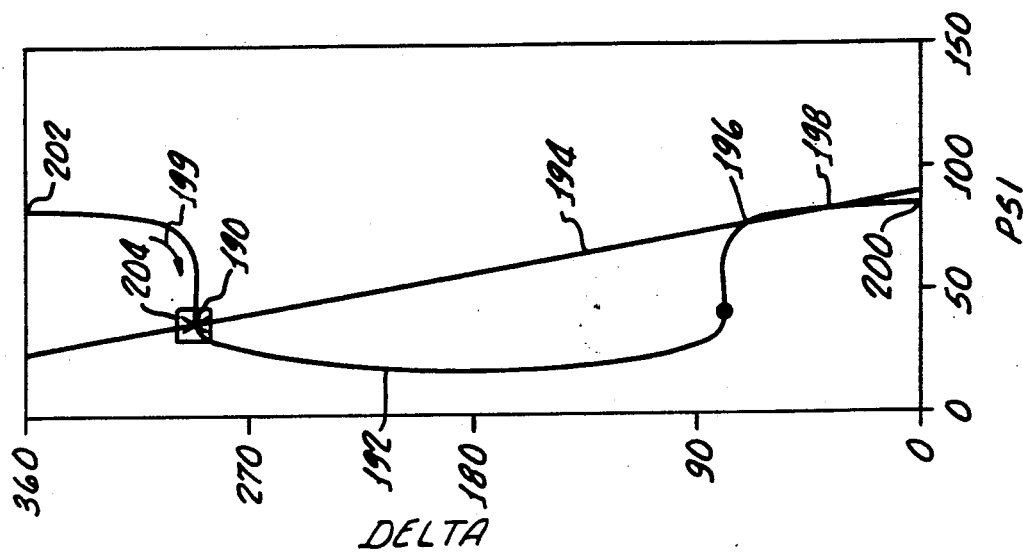
FIGS. 5a through 5c illustrate delta and psi loci of double layer transparent film models and endpoint crossing lines therefor.
Figure 5B:
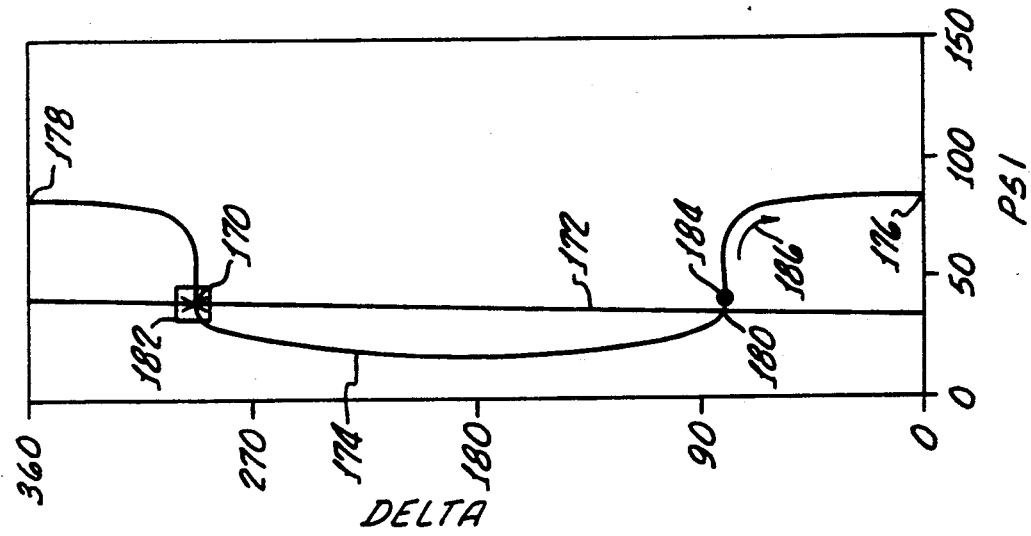
Figure 5A:
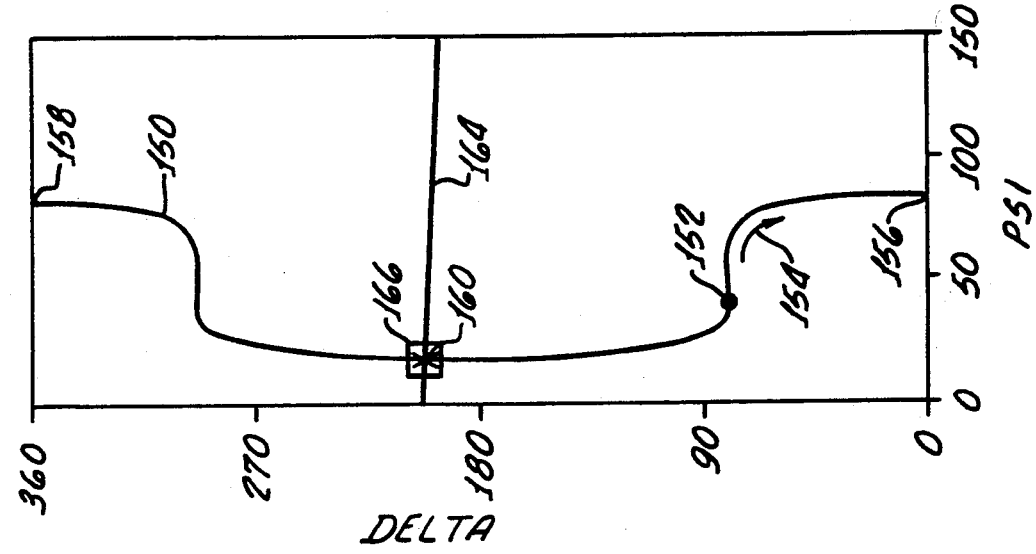

FIGS. 5a, 5b and 5c demonstrate delta-psi loci of a double layer film model of a silicon nitride deposited on 1,000 Angstroms of silicon dioxide film, which itself has been deposited upon a silicon substrate. FIG. 5a illustrates the locus 150 as an open shaped curve which starts at a point 152 at which there is no nitride film. Data points move in the direction of arrow 154 and have a discontinuity point at 156, at which time the locus continues at the upper end of the figure, at point 158. Cycle thickness for this model is 1866 Angstroms. In FIG. 5a the desired endpoint 160 is 1006 Angstroms. The unbounded control line 164, established as previously discussed, intersects the locus only once per cycle. However, the above described control method will detect a sign change in ERROR at the discontinuity point 156 since the data at this point jump across the line 164 to the point 158 at the upper portion of the curve. A range check, as previously described in connection with FIG. 4, is illustrated in FIG. 5a by box 166. Use of this range check, together with the sign change, will readily prevent use of the discontinuity point 156 (at which the ERROR changes sign) as the stopping point.

In FIG. 5b an endpoint 170 has been set for a nitride film thickness of 332 Angstroms. The unbounded control line 172 of FIG. 5b intersects the measured Dm, Pm curve 174 twice per cycle. The curve 174 has a first discontinuity point 176, which is a lower point in this drawing, at which it switches to an upper discontinuity point 178. Both of these discontinuity points are on the same side of the unbounded line 172, and thus there is no sign change at either of these discontinuity points. Note however that the unbounded control line 172 is still transverse to the direction of the data point curve 174 at the selected endpoint 170. The curve 174 does cross the control line 172 at a second crossing point 180 (and ERROR again changes sign), and thus it is necessary to employ a range check box 182 as previously described to distinguish between the two points 170 and 180 at which the ERROR sign changes. In FIG. 5b point 184 indicates the starting point with the data points moving in the direction of arrow 186.

In the process depicted in FIG. 5c the thickness at a selected endpoint 190 is 364 Angstroms for the silicon nitride, and the curve 192 defining the locus of measured Dm and Pm points intersects the unbounded control line 194 at three points, namely the endpoint 190 and at additional points 196 and 198. Moreover, the curve, which moves in the direction of arrow 199, has a discontinuity at point 200, at the lower end of the graph, at which point it jumps to the upper end of the graph, point 202. Again, a range check, indicated by range check box 204 around the endpoint 190, is employed to allow the process to continue when the measured data points cross the control line 194 at points such as 196 and 198, which are not the desired endpoints. Further, in this curve, the discontinuity point 200 is on the side of the line opposite that of the discontinuity point 202 so that an additional sign change (again not indicative of the endpoint) occurs here. Thus, in FIG. 5c, as in the previously described process runs, the method includes the counting of repetitive cycles of the delta-psi locus and the making of a range check upon the occurrence of each sign change so that only that sign change which occurs within the selected range and also within the predetermined cycle number is used to stop the process.

The arrangement illustrated in connection with FIG. 3 for determining the unbounded control line is presently preferred. However, it will be readily appreciated that many different methods may be employed to determine such a line or an equivalent line. For example, after having determined an endpoint 70, which is the desired endpoint at a given temperature (such as 1,100° C. for example), one can determine a second endpoint identifying a film of the same thickness as that identified by endpoint 70 but which second endpoint would occur at a different temperature, such as 1,000° C., for example. Then an unbounded control line would be defined by the line extending through the two endpoints that had been calculated for the same film thickness but at different temperatures. Expanding on this second method of developing and defining the unbounded control line 100 one could precalculate delta and psi coordinates of three or more endpoints, each of the same desired target thickness but each at a different temperature, and then a best fit line, drawn through all of these endpoints, would define the desired control line. Further, the control need not be a straight line, but may have some curvature. Control lines defined by these other methods are utilized in the same way as described in connection with control line 100. That is, a function is defined which has a value of zero for points on the control line. For each point identified by a pair of measured coordinates as the film thickness changes the function is computed. As previously described, when the value of the computed function for a measured point changes sign, the process target thickness has been reached, and the process is terminated.

It is important to note that the use of the sign change as a signal to identify the time of process termination has the advantage of providing a clear, reliable and repeatable signal that is less likely to be affected by process variables and spurious electronic noise in the system. Further, by employing a function of the measured coordinates that is equal to zero when the coordinates define a point on the control line, there is effectively being calculated a perpendicular distance from the control line to the point defined by the measured coordinates Thus, from one point of view, the method may be considered to include the defining of an unbounded control line by any one of the methods previously described, computing, for each point defined by a pair of measured delta and psi coordinates, a distance from such measured point to the unbounded control line and perpendicular thereto, and then determining when such distance becomes substantially zero. Note that such a distance from the measured point to the control line has one sign when the measured point is on one side of the control line and an opposite sign when the measured point has crossed the control line and is on the other side of the control line. Accordingly, the time of occurrence of a change of sign of the distance is a clear, repeatable and unambiguous indication of attainment of process termination time.

The method of endpoint control described above is carried out in conjunction with the overall process control by a suitably programmed computer having communication interface with the reactor controller 40 of FIG. 1 and with the ellipsometer controller 54. The control algorithm employed by the endpoint controller 56 of FIG. 1 is illustrated in the flow chart of FIG. 6a and 6b. The endpoint (De and Pe), the second point (Ds and Ps), and the cycle number (CYCLEN) required for the endpoint thickness are all entered into the endpoint controller through the input device, as indicated in block 230, FIG. 6a. The endpoint line calculation is performed as indicated in block 232 for use in the calculation of ERROR according to Equation (6). The endpoint controller then waits for a signal from reactor controller 40, see also FIG. 1, to start the endpoint checking and control process as indicated in block 234. NEWK (the current ERROR) and CYCLE are zeroed, block 236 and OLDK (previous ERROR) is set equal to NEWK in block 238. The controller then checks the abort status, as indicated in block 240, for the possibility of a command coming from the reactor controller 40 or an alarm status from the ellipsometer 54 that warrants an immediate stop, as indicated at block 242. If such a signal occurs, the endpoint check is stopped, via a line 243, and the system goes into abort status. If there is no abort signal, the endpoint controller requests and receives delta and psi values from ellipsometer 54, as indicted in block 244, and calculates NEWK (current ERROR) in accordance with Equation (6) from the measured values received from the ellipsometer The ERROR calculation is indicated in block 246. The system then looks for a sign change, block 248 (FIG. 6b), to determine if OLDK and NEWK have the same or different algebraic signs. If there is no sign change the current error NEWK is then stored (via line 249) by setting OLDK to NEWK in block 238. This loop then continues, reading each new set of measured values at the selected time intervals, performing the calculation of ERROR, and checking for sign change. Repetition of this loop stops if there is a sign change, which may indicate that a crossing of the unbounded control line has occurred The controller will then make a further check to determine if the delta and psi coordinates most recently read are in the correct range, as indicated at block 250. If the measured coordinates are not within the correct range, the most recently calculated ERROR NEWK is stored, via line 249, as OLDK, block 238, and the process of the flow chart repeats.

If a sign change has occurred, and, in addition, the most recently measured values are within the range of the range check, the controller determines if the cycle count CYCLE is the same as the cycle number, CYCLEN, required for the selected endpoint, as indicated in block 252. If the proper number of cycles have not occurred, the cycle count is augmented by one, as indicated in block 254, and the most recently calculated error value NEWK is stored, via line 249, as in block 238, and the loop continues. If the proper number of cycles have occurred (with a sign change, and within the range check), then CYCLE=CYCLEN, and the process has reached its desired endpoint, as indicated at block 256. The system then signals that the endpoint or desired stop point has been reached, block 258. The system signals the stop point has been reached by sending a signal to the reactor controller 40, via a line 259, which terminates the process.

Figure 6A:
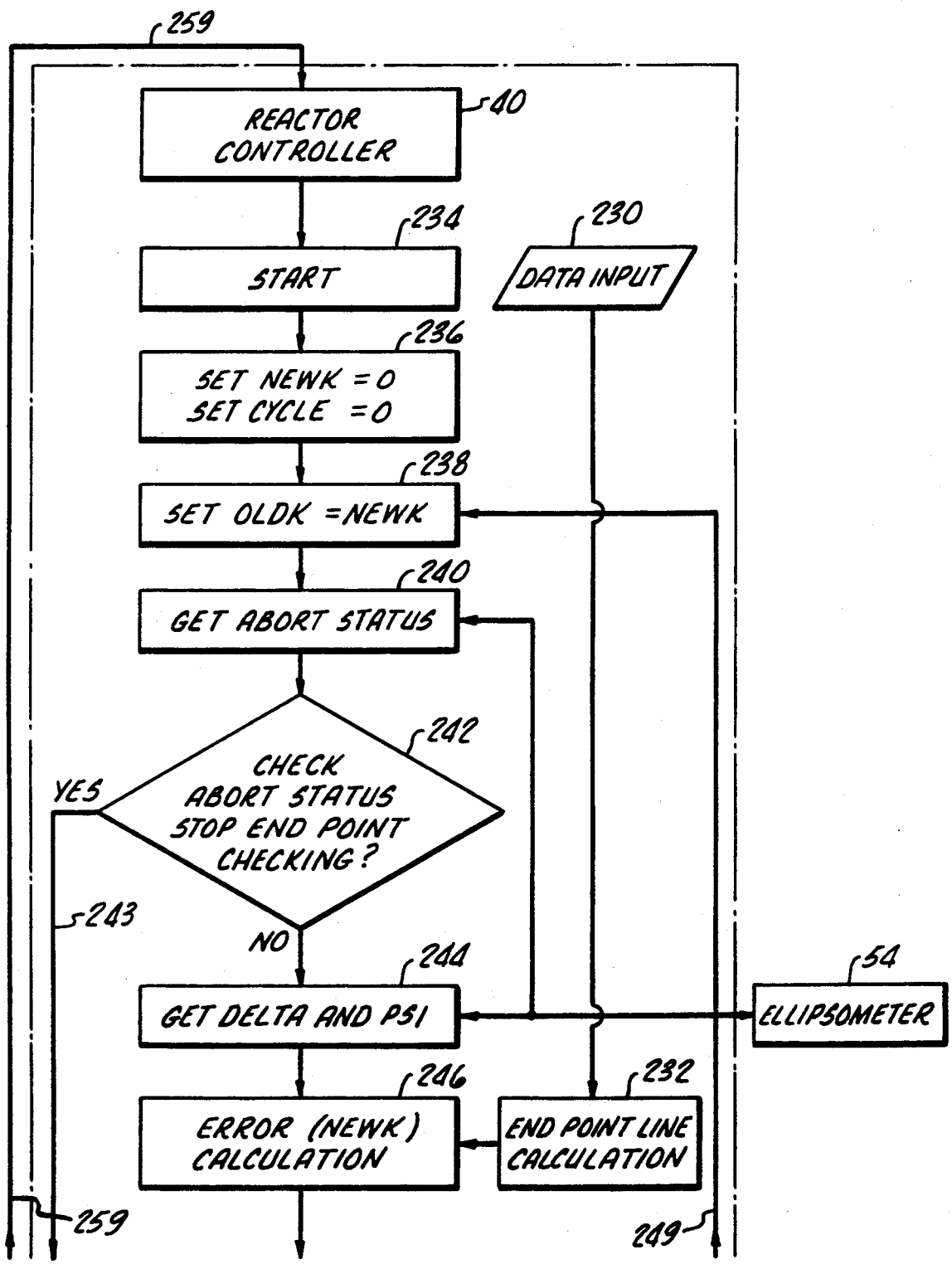
FIGS. 6a and 6b comprise a flow chart of an in-situ ellipsometer endpoint control program employed in the present invention.
Figure 6B:
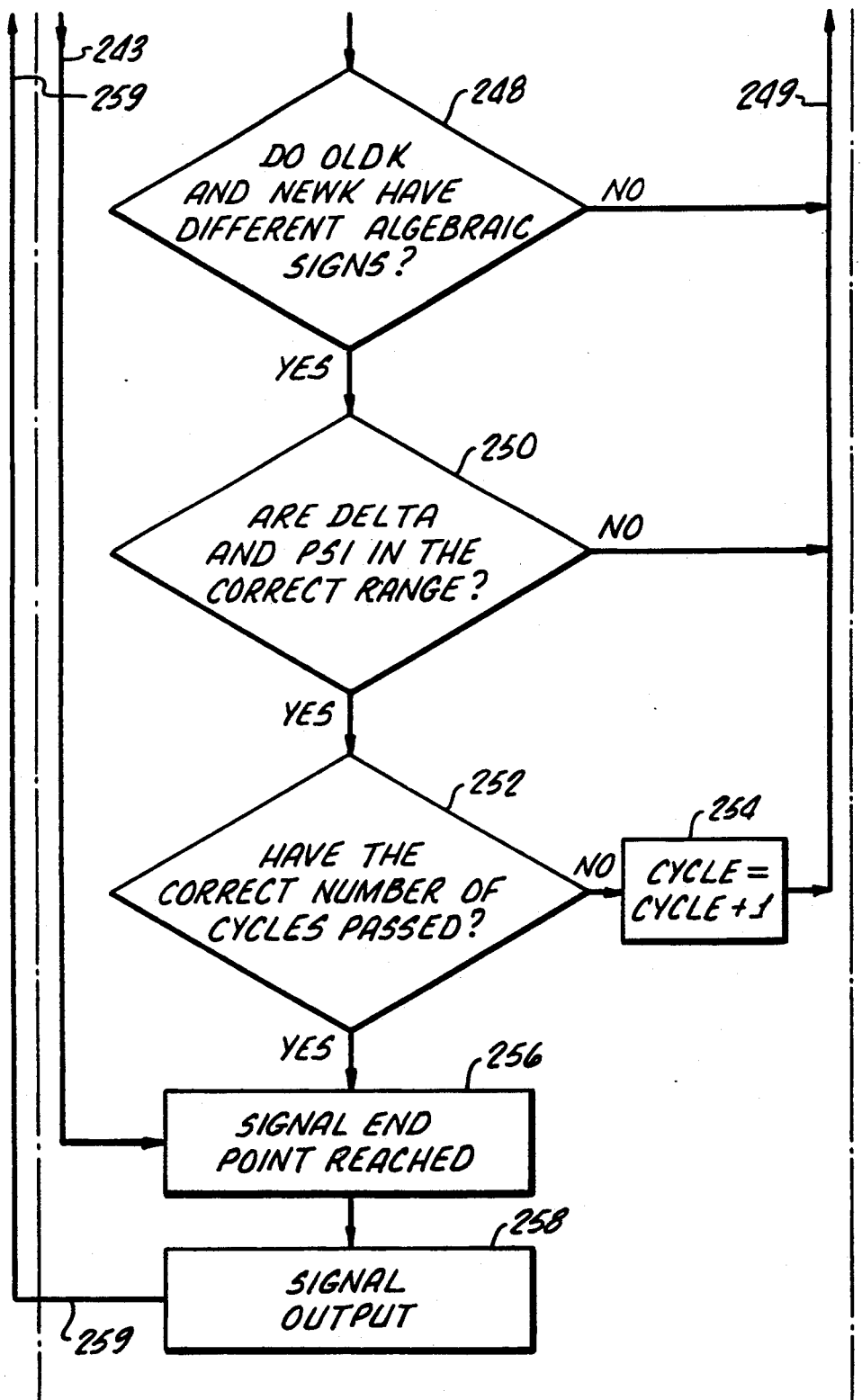

The process described in connection with the flow chart of FIGS. 6a and 6b has been carried out with apparatus of the type illustrated in FIG. 1 to perform an oxide growth process on a silicon substrate. A plurality of such process runs clearly verified validity and repeatability of the described method. In these process runs a silicon wafer was placed within the chamber of reactor 12 (FIG. 1) under atmospheric pressure with the reactor walls unheated. With the chamber filled with inert gas at ambient pressure, the wafer temperature was quickly brought up to 1,100° C., by the lamps 14,16, at a temperature ramp rate of 100° C. per second. After a suitable temperature stabilization period, oxygen was introduced into the chamber from the gas delivery system 44 at a flow rate of 500 standard cc per minute to allow growth of the oxidation film silicon wafer. At the same time the endpoint controller was turned on. Endpoint data, which is delta =105.167 and psi=23.088 was calculated for a 400 Angstrom silicon dioxide film from the parameters described above in connection with the graph of FIG. 3. Process temperature was monitored by the pyrometer 26 and the illustrated feedback control of the lamps. The in-situ ellipsometer 46,50,54 monitored the film thickness at the center point of the wafer for endpoint control. When the process reached the endpoint, as determined by the endpoint controller 56 in accordance with the steps illustrated in the flow chart of FIGS. 6a and 6b, the oxygen gas and lamps were turned off and wafer temperature was rapidly ramped down to room temperature. Thereafter, at room temperature, the oxide film thickness data was measured at the center point of the wafer with a second, different ellipsometer.

Figure 7:
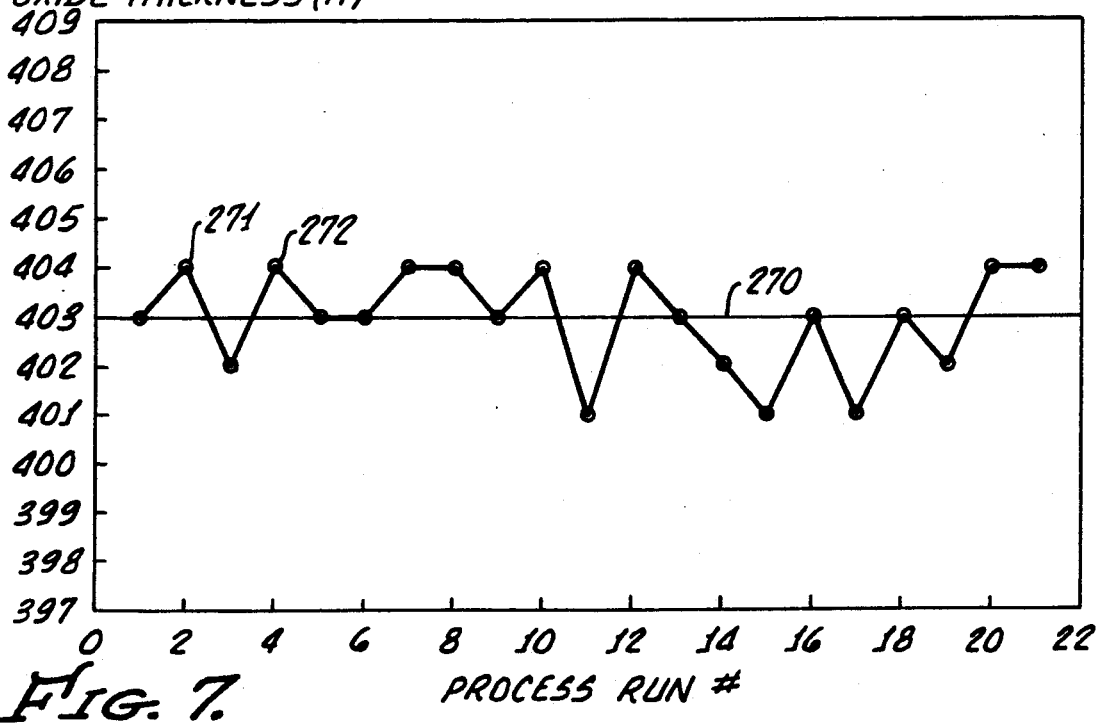
FIG. 7 is a graph showing final film thickness results of a number of repetitions of film grown process runs in a single wafer RTP reactor utilizing an endpoint control method incorporating principles of the present invention.

FIG. 7 is a graph illustrating the final film thickness of oxide films attained in twenty-one repeated oxidation runs, each of which was as nearly identical as possible In FIG. 7, line 270 illustrates an average film thickness of 403 Angstroms, as compared to the desired or target thickness of 400 Angstroms. The various points, such as 271, 272, etc. illustrate film thicknesses attained at respective ones of the individual process runs that were performed with (intended) identical parameters, and under (intended) identical conditions. The results show that an average film thickness of 403 Angstroms was attained with a standard deviation of 1 Angstrom. The average index of refraction measured for the oxide film was 1.455, with a standard deviation of 0.001. Deviation of the average thickness 403 Angstroms from the target thickness 400 Angstroms is attributable to system calibration errors, such as deviations associated with the index of refraction of the film at the process temperature, the angle of incidence, and the like. Other factors contributed to this deviation, including measurement errors between the two ellipsometers, one of which was used for in-situ control and the other for final measurement. In addition, some residual film growth occurs on hot wafers after process termination. The small standard deviation, which is less than 0.25% clearly evidences the excellent repeatability of the described control method.

The described endpoint control method is applicable to many different types of film growth and removal processes, including the deposition of various optical coatings It is also useful in diamond film growth, magnetic recording film deposition (sputtering), solar cell wafer processing, CD ROM film processing, refractory coatings, ceramic films, polymer films, and MBE (molecular beam epitaxy) films of the type described in an article entitled "Surface Analysis During Vapor Phase Growth", by F. Hottier and J. B. Theeten, in Journal of Crystal Growth 48 (1980), pages 644-654.

The described method has been initially employed in film growth processes for growth of silicon dioxide on silicon wafers, employing the rapid thermal processing equipment illustrated in FIG. 1. This method has the unique advantage, when used in a rapid thermal processing method, of enabling control of final film thickness substantially independent of temperature variation. As previously mentioned, particularly for rapid thermal processing equipment, control of the process employing fixed time is highly unreliable because film growth rates are critically dependent upon the actual temperature of the wafer and the ability of the controller to hold that temperature. In a second set of process runs, the apparatus of FIG. 1, employing the endpoint control method described herein, was used to grow 100 Angstroms silicon dioxide film on a 100 millimeter diameter silicon wafer using 0.5 standard liters per minute of oxygen gas under atmospheric pressure conditions. The process, with other parameters otherwise identical, was repeated for 1,100° C. temperature and 1,000° C. temperature, with the process run according to the conditions described above. In both cases film growth reactions were terminated at the first points after crossing the unbounded control line (e.g., upon occurrence of a sign change in ERROR), followed by a rapid cooling process step. Wafers were removed from the chamber, and film thickness data was measured at the center point of the wafer with a second ellipsometer after each process run. Results of five process runs at 1,100° C. showed an average film thickness of 95.3 Angstroms, with a standard deviation of 0.9 Angstroms, and for process runs at 1,000° C., results showed an average film thickness of 96.2 Angstroms, with a standard deviation of 1.1 Angstrom. These results demonstrate that this method is capable of producing desired process results to within 1 Angstrom of thickness difference, even with a temperature deviation of 100° C. (96.2 as against 95.3 Angstroms). In prior art methods such a large temperature difference might cause major errors or an indeterminate process termination. Furthermore, upon increasing the intended final film thickness by 4 Angstroms, test runs of the described system and method at 1,100° C. provided an average film thickness of 98.9 Angstroms, with a standard deviation of 1.0 Angstrom. This is an increase of 3.6 Angstrom, which is very nearly equal to the specified 4 Angstrom increase, thus demonstrating that the control system can be calibrated to produce accurate results.

There have been described methods and apparatus for endpoint control to obtain a desired film thickness which provide superior accuracy, repeatability and control of film thickness in processes for film growth or etching.

The foregoing detailed description is to be clearly understood as given by way of illustration and example only, the spirit and scope of this invention being limited solely by the appended claims.

What is claimed is:

1. A method of control of thickness of a film on a substrate comprising the steps of:
   positioning the substrate in a chamber,
   controlling environment in said chamber to change thickness of a film on the substrate,
   employing an ellipsometer to measure delta and psi coordinates of said film,
   determining delta and psi coordinates of an endpoint of desired thickness,
   defining a control line through said endpoint in accordance with the equation $A(D_e) + B(P_e) + C = 0$ wherein A, B, and C are constants of an unbounded line passing through the endpoint, and $D_e$ and $P_e$ are the delta and psi coordinates of said endpoint.
   reading measured delta and psi coordinates to define measurement points as thickness of said film changes,
   determining the relation between said control line and said measurement points, and
   terminating change in said film thickness in response to said relation.

2. The method of claim 1 wherein said step of determining the relation between said control line and measurement points comprises defining an error in accordance with said equation.

3. The method of claim 2 wherein sad step of terminating comprises detecting a change in sign of said error.

4. The method of claim 3 including making a range check when a change in sign is sensed, and wherein said terminating step is performed in response to results of said range check.

5. The method of claim 2 wherein said control line is defined as a straight line through said endpoint and transverse to a line between said endpoint and a second point of thickness different than said endpoint thickness.

6. The method of claim 1 wherein said delta and psi coordinates vary cyclically as said film thickness varies, and including counting cycles of variation of said delta and psi coordinates, said step of terminating being performed upon count of a predetermined number of cycles.

7. A method for controlling thickness of a film or film portion on a substrate comprising the steps of:
   positioning the substrate in a chamber, controlling environment in said chamber to cause a change in thickness of a film on said substrate, said substrate and film thereon comprising a workpiece on which film is to be deposited or at least partially removed, employing ellipsometry to measure delta and psi coordinates of said film, said step of measuring comprising:

directing light at said workpiece as said film thickness is changed, and receiving light reflected from said workpiece, determining delta and psi coordinates of an endpoint representing a predetermined target film thickness, defining a control line through said endpoint and transverse to the direction of a plot of delta and psi coordinates of points representing film thickness near said endpoint, said last mentioned step comprising defining a control line through said endpoint in accordance with the equation $A(D_e) + B(P_e) + C = 0$ wherein A, B, and C are constants of an unbounded line passing through the endpoint, and $D_e$ and $P_e$ are the measured delta and psi coordinates of said endpoint, generating an error indicative of a relation between said line and points defined by said measured coordinates, and employing said error to terminate change in film thickness.

8. The method of claim 7 wherein a film of said predetermined thickness is deposited on said substrate.

9. The method of claim 7 wherein a film on said substrate is at least partially etched to said predetermined thickness.

10. The method of claim 7 wherein said step of controlling environment comprises heating said substrate, and including the step of rapidly decreasing temperature of said wafer upon said step of terminating change in film thickness.

11. The method of claim 7 wherein said step of defining a control line comprises determining delta and psi coordinates of a second point having a thickness close to said predetermined thickness, and wherein said step of defining a control line further comprises defining such line in a direction substantially perpendicular to a line between said endpoint and said second point.

12. The method of claim 7 wherein said substrate comprises a semiconductor wafer and said chamber comprises an elongate kaleidoscope, said step of positioning the substrate comprising positioning said wafer in said kaleidoscope with the wafer transverse to the axis of said kaleidoscope.

13. The method of claim 12 wherein said step of controlling environment includes the step of rapidly heating said wafer in said kaleidoscope to a predetermined temperature, flowing into said kaleidoscope a gas that acts at said temperature to cause a change in thickness of film on said wafer, and including the step of rapidly decreasing temperature of wafer upon said step of terminating change in film thickness.

14. The method of claim 7 wherein said step of generating an error includes the step of sensing a change of sign of the error, and wherein occurrence of change in sign is employed to terminate change in film thickness.

15. The method of claim 14 including the step of making a range check when a change in sign is sensed and wherein said step of terminating is performed in response to results of said range check.

16. The method of claim 14 wherein said terminating step is performed only when said sensed change of sign occurs at a point within a predetermined range of said endpoint.

17. The method of claim 7 wherein said delta and psi coordinates vary cyclicly as said film thickness varies, and including the step of counting cycles of variation of said delta and psi coordinates, said step of terminating being performed upon a count of a predetermined number of said cycles.

18. A method for controlling thickness of film on a substrate comprising the steps of:

positioning the substrate in a chamber, controlling environment within said chamber to cause a change in thickness of film on said substrate, employing ellipsometry to measure delta and psi coordinates of said film, determining delta and psi coordinates of an endpoint of desired thickness, defining a control line through said endpoint in accordance with the equation $A(D_e) + B(_e) + C = 0$ wherein A, B, and C are constants of an unbounded line passing through the endpoint, and $D_e$ and $P_e$ are the delta and psi coordinates of said endpoint, said control line being a function of delta and psi that is zero for points on said control line passing through said endpoint and extending transverse to a plot of points of measured delta and psi coordinates near said endpoint generating an error that represents said function of measured delta and psi coordinates, and employing said error to signal attainment of said endpoint of desired thickness.

19. The method of claim 18 wherein said step of employing comprises sensing sign of said error and terminating said process upon occurrence of a change in sign of said error.

20. The method of claim 18 wherein said attainment of the endpoint of desired thickness is signalled upon occurrence of a change in sign of said error while the film thickness is within a predetermined range of said desired film thickness.

21. The method of claim 18 wherein said delta and psi coordinates vary cyclicly as film thickness varies, and wherein said step of signaling attainment of said endpoint of desired thickness is carried out when said error changes sign within a selected cycle of the cyclic variation of said delta and psi coordinates.

22. The method of claim 18 wherein said substrate is a silicon wafer and wherein said wafer is heated in inert gas at atmospheric pressure, at a rate of temperature increase of about 100° C. per second, and including the step of flowing oxygen into the chamber.

23. A method of controlling thickness of a film or film portion on a substrate comprising the steps of:

positioning the substrate in a chamber, controlling environment within said chamber to cause thickness of said film to change, measuring ellipsometric parameters of said film as said film thickness changes, thereby defining points related to thickness of said film, defining, in a plane of said parameters, an unbounded line having a predetermined relation to a desired endpoint of target thickness of said film in accordance with the equation defining a control line through said endpoint that is defined by he equation $A(D_e) + B(P_e) + C = 0$ wherein A, B, and C are constants of an unbounded line passing through the endpoint, and $D_e$ and $P_e$ are the delta and psi coordinates of said endpoint and terminating the changing of film thickness when measured parameters have a predetermined relation to said unbounded line.

24. The method of claim 23 wherein said line passes through an endpoint representing said target thickness.

25. The method of claim 23 wherein said step of controlling environment in said chamber comprises heating the substrate to a temperature within a range appropriate for depositing or etching film on the substrate, and introducing into said chamber a gas that acts at said temperature to cause a change in thickness of a film on said substrate.

26. The method of claim 25 wherein said substrate is a silicon wafer, and said process is carried out by heating said semiconductor wafer in an elongated kaleidoscope with said wafer positioned transverse to the axis of the kaleidoscope.

27. A method of controlling thickness of a film on a substrate comprising the steps of:

subjecting the substrate to an environment that causes a change in thickness of film on the substrate, reflecting light from said film, repetitively measuring first and second ellipsometric parameters of light reflected from said film that define coordinates of points related to a film thickness endpoint, generating, in a coordinated system of said parameters, a locus of points for which a predetermined function of said first and second parameters is substantially zero, said step of generating comprising defining a control line through said endpoint in accordance with the equation $A (D_e) + B (P_e) + C = 0$ wherein A, B, and C are constants of an unbounded line passing through the endpoint, and $D_e$ and $P_e$ are the delta and psi coordinates of said endpoint, generating an error indicative of the relation between points defined by pairs of measured parameters and said locus, and employing said error to terminate change of thickness of the film.

28. The method of claim 27 wherein said error is generated as values of said function for pairs of said measured parameters.

29. The method of claim 27 wherein said step of employing said error comprises detecting change of sign of said error.

30. The method of claim 27 including the step of generating an error equal to $A (D_m) + B (P_m) + C$, sensing a change in algebraic sign of said error, and terminating said change in thickness when (a) said algebraic sign changes, and (b) said measured parameters are within a predetermined range of delta and psi coordinates of said endpoint.

31. The method of claim 27 wherein said film is silicon dioxide to be grown on the substrate, and wherein said substrate comprises a silicon wafer, and including the steps of positioning said wafer within an elongated kaleidoscope with said wafer transverse to the kaleidoscope axis, introducing a gas into said chamber, rapidly raising the temperature of said wafer to a point at which the gas reacts with the wafer, and terminating growth of the film by rapidly lowering the temperature of said wafer.

32. Apparatus for rapid thermal processing of a workpiece comprising:

a processing chamber, heater means for raising the temperature of a workpiece in said chamber, means in said chamber for supporting a workpiece to be heated by said heating means, means for introducing gas into said chamber, an ellipsometer comprising:

polarizer module means for directing a polarized light beam into said chamber to a point on a workpiece supported on said workpiece support means, analyzer module means or receiving light reflected from a workpiece mounted on said workpiece support means, ellipsometer control means for generating measured delta and psi coordinates of light received by said analyzer module means, and endpoint control means responsive to said ellipsometer control means for receiving delta and psi coordinates measured by said ellipsometer during processing of a heated workpiece within said chamber, said endpoint control means comprising:

means for defining a control line through a target endpoint of desired thickness in accordance with the equation $A (D_e) + B (P_e) + C = 0$ wherein A, B, and C are constants of an unbounded line passing through the endpoint, and $D_e$ and $P_e$ are the delta and psi coordinates of said endpoint, detecting means for detecting a relation between a pair of measured delta and psi coordinates and said control line, and means responsive to said detecting means for providing an end of process signal.

33. The apparatus of claim 32 including means for determining delta and psi coordinates of said target endpoint of desired thickness, said means for defining said control line comprising means for defining said control line transverse to the direction of a plot of delta and psi coordinates of thickness at said endpoint, means for generating an error indicative of a relation of said control line to a point defined by said measured delta and psi coordinates, and means responsive to said error for terminating change in film thickness.

34. The apparatus of claim 33 wherein said means for terminating comprises means for rapidly decreasing temperature of said substrate.

35. The apparatus of claim 34 wherein said chamber comprises an elongated kaleidoscope.

36. Rapid thermal processing apparatus comprising:

lamp means, means to support a workpiece, and means to optically couple said lamp means to a workpiece supported on said workpiece support means, to effect relatively uniform heating of said workpiece, said optical coupling means being a hollow, integrating light pipe that extends at lest substantially to said workpiece support means and that causes the intensity of light from said lamp means to be relatively uniform across said light pipe at said workpiece, said lamp means being disposed within said light pipe, the aspect ratio in aid light pipe being at least 1, means for directing a beam of polarized light at a workpiece on said workpiece support means, means for receiving polarized light reflected from said workpiece, ellipsometric means for computer delta and psi ellipsometric coordinates of received light reflected from said workpiece, means for determining delta and psi ellipsometric coordinates of a target endpoint of desired thickness of a film on aid substrate, means for defining a control line through said target endpoint transverse to the direction of a plot of delta and psi coordinates of film thickness at said endpoint in accordance with the equation $A(D_e)+B(P_e)+C=0$ wherein A, B, and C are constants of an unbounded line passing through the endpoint, and $D_e$ and $P_e$ are the delta and psi coordinates of said endpoint, means for reading measured delta and psi coordinates as thickness of film on said substrate is varied, means for generating an error signal representing a relation between said line and said measured coordinates, means for sensing a change in sign of said error signal, means for generating a stop signal in response to a sensed change of said sign, and means for deenergizing said lamp means and rapidly decreasing temperature of said substrate upon occurrence of said change of sign.

37. The apparatus of claim 36 wherein said workpiece comprises a silicon wafer, wherein said lamp means comprises means for increasing the temperature of said wafer at the rate of about 100° C. per second to a temperature in the order of about 1,000° C., and further including means for flowing oxygen into said chamber.

* * * * *